United States Patent [19]

Tomihata et al.

[11] Patent Number: 5,797,962
[45] Date of Patent: Aug. 25, 1998

[54] SURGICAL SUTURE AND METHOD FOR PREPARATION THEREOF

[75] Inventors: Kenji Tomihata; Ikuo Sasaki; Masakazu Suzuki, all of Ayabe, Japan

[73] Assignee: Gunze Limited, Kyoto-fu, Japan

[21] Appl. No.: 654,105

[22] Filed: May 28, 1996

[30] Foreign Application Priority Data

May 25, 1995 [JP] Japan .................. 7-152596

[51] Int. Cl.$^6$ .................. A61B 17/04
[52] U.S. Cl. .................. 606/228; 606/230
[58] Field of Search .................. 606/228, 230, 606/231, 229

[56] References Cited

U.S. PATENT DOCUMENTS

| | | |
|---|---|---|
| 4,057,537 | 11/1977 | Sinclair . |
| 4,300,565 | 11/1981 | Rosensaft et al. . |
| 4,605,730 | 8/1986 | Shalaby et al. . |
| 5,007,922 | 4/1991 | Chen et al. ............ 606/228 |
| 5,279,783 | 1/1994 | Liu et al. ............ 606/228 |

FOREIGN PATENT DOCUMENTS

| | | |
|---|---|---|
| 58-642383 | 7/1983 | Japan . |
| 63-64988 | 12/1984 | Japan . |
| 64-56055 | 8/1987 | Japan . |
| 63-74418 | 10/1988 | Japan . |

*Primary Examiner*—Michael Buiz
*Assistant Examiner*—Kevin Truong
*Attorney, Agent, or Firm*—Knobbe, Martens, Olson & Bear, LLP

[57] ABSTRACT

The invention relates to a surgical suture comprising a copolymer as an essential component, the copolymer consisting of lactic acid (lactide) and ε-caprolacton as repeating unit, wherein shrinkage ratio of said surgical suture is 5% or less after heat treatment at 60° C. for 20 hours and method for production thereof.

18 Claims, 3 Drawing Sheets

SURGICAL SUTURE AND METHOD FOR PREPARATION THEREOF

FIELD OF THE INVENTION

The present invention relates to a surgical suture and a method for preparing the suture.

BACKGROUND OF THE INVENTION

A polymer of lactic acid (lactide), and a copolymer of lactic acid (lactide) and the other biodegradable monomer are hydrolyzed in vivo and absorbed. These polymers are applied to biomaterials as follows. For example, biodegradable polymers are utilized as microsphere for DDS; antiadhesive material in the form of film; a guide tube for regeneration of peripheral nerve; and a surgical suture. In particular, several bioabsorbable surgical sutures made of glycolic acid homopolymer or copolymer chiefly consisting of glycolic acid are on the market. Because of stiffness of polylactic acid (polylactide), polyglycolic acid and like bioabsorbable materials, however, said bioabsorbable materials are difficult to use as a monofilament. Therefore, the bioabsorbable materials are used as braided multifilament to impart flexibility to the material.

However, a suture prepared by braiding a number of multifilament has disadvantages of complicated manufacturing process, higher risk of microorganism infection, etc.

Production of suture consisting of monofilament has been tried in a variety of ways so as to solve said problems and cut costs. Such sutures consisting of monofilament are inferior in workability such as flexibility and ease of knot formation, as well as strength required as suture.

Because melt spinning is not suitable for copolymer of lactic acid (lactide), wet spinning of copolymer of lactic acid (lactide) is tried after dissolving copolymer of lactic acid (lactide) in an organic solvent (Japanese Unexamined Patent Publication 64-56055).

However, complete removal of solvent from monofilament suture produced by wet spinning is very difficult. The suture is inferior in uniformity due to existence of solvent within the suture. Specifically, such suture is likely to be infected by bacteria due to ease of concave and convex formation. Such suture is also likely to be broken due to slip-resistant characteristics during knot formation. In addition, the suture has low breaking strength and requires a large amount of agent for coagulating bath.

It is an object of the invention to provide a monofilament suture for medical use with improved economy and performance.

It is another object of the invention to provide a multifilament suture with improved productivity.

It is another object of the invention to provide a method for producing monofilament suture made of copolymer containing lactic acid (lactide) with outstanding flexibility and smooth handling as well as required strength.

BRIEF DESCRIPTION OF THE DRAWINGS

FIG. 1A shows step A of melt-spinning and drawing a copolymer in hot water, in which the water bath temperature is 60°–90° C., and the draw ratio is 8–12. The copolymer is wound and then stored. FIG. 1B shows step B of redrawing the copolymer obtained in step A, in which the draw ratio is 1.2–1.5, and the temperature of an oven chamber is 90°–140° C. The copolymer is wound and then stored. FIG. 1C shows step C of heating the copolymer obtained in step B while exerting tension thereon, in which heat treatment is conducted at 90°–130° C. for 0.2–24 hours after rewinding the copolymer. The copolymer is then stored. FIG. 1D shows step D of relaxing the copolymer obtained in step C, in which relaxation treatment is conducted at 60°–110° C. for 0.2–20 hours after unfastening the copolymer from a bobbin. The copolymer is then wound around a bobbin to store the copolymer as the final product.

DISCLOSURE OF THE INVENTION

Figure 1A:
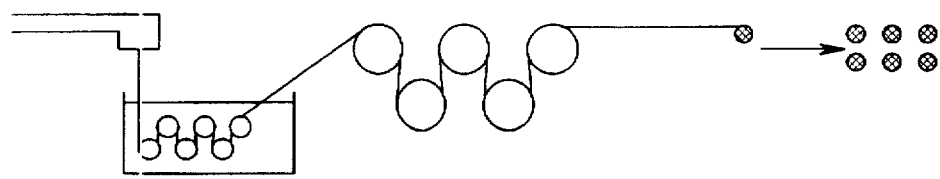
FIGS. 1A through 1D are each a schematic view showing each step of a method of the invention.

The present invention relates to the following surgical suture and method for preparing the suture.

Item 1. A surgical suture comprising a copolymer as an essential component, the copolymer consisting of lactic acid (lactide) and ε-caprolacton as repeating unit, wherein shrinkage ratio of said surgical suture is 5% or less after heat treatment at 60° C. for 20 hours.

Item 2. The surgical suture according to item 1 wherein molecular weight of said suture determined by GPC ranges from about 100,000 to 250,000.

Item 3. The surgical suture according to item 1 wherein lactic acid (lactide) has a molar ratio of about 99.9-50 mole % and ε-caprolacton has a molar ratio of about 0.1–50 mole %, when taking total molar ratio of lactic acid (lactide) and ε-caprolacton as 100 mole %.

Item 4. The surgical suture according to item 1 wherein tensile strength of said suture is at least 2.5 g/d.

Item 5. The surgical suture according to item 1 wherein knot-pull strength of said suture is at least 2.0 g/d.

Item 6. The surgical suture according to item 1 wherein elongation at break of said suture is 50±10%.

Item 7. The surgical suture according to item 1 wherein knot-pull elongation at break of said suture is 45±10%.

Item 8. The surgical suture according to item 1 wherein said suture is monofilament.

Item 9. The surgical suture according to item 1 wherein said suture is multifilament.

Item 10. The method for producing surgical suture comprising the steps of:

(i) melt-spinning a copolymer consisting of lactic acid (lactide) and ε-caprolacton as repeating unit; and (ii) drawing the melt-spinned copolymer of step (i) in hot water.

Item 11. The method for producing surgical suture according to item 10 comprising the steps of:

(i) melt-spinning a copolymer consisting of lactic acid (lactide) and e-caprolacton as repeating unit;

(ii) drawing the melt-spinned copolymer of step (i) in hot water and (iii) redrawing the polymer drawn in step (ii).

Item 12. The method for producing surgical suture according to item 10 comprising the steps of:

(i) melt-spinning a copolymer consisting of lactic acid (lactide) and ε-caprolacton as repeating unit;

(ii) drawing the melt-spinned copolymer of step (i) in hot water;

(iii) redrawing the polymer of step (ii); and (iv) heat treatment of the redrawed copolymer of step (iii).

Item 13. The method for producing surgical suture according to item 10 comprising the steps of (i) melt-spinning a copolymer consisting of lactic acid (lactide) and e-caprolacton as repeating unit;

(ii) drawing the melt-spinned copolymer of step (i) in hot water;

(iii) redrawing the polymer of step (ii);

(iv) heat treatment of the copolymer of step (iii); and (v) relaxation treatment of copolymer of step (iv).

Item 14. The method for producing surgical suture according to item 10 wherein said drawing step (ii) in hot water is carried out at 60°–90° C. under draw ratio of 8–12 times.

Item 15. The method for producing surgical suture according to item 11 wherein said redrawing step (iii) is carried out at 90°–140° C. under draw ratio of 1.2–2.5 times.

Item 16. The method for producing surgical suture according to item 12 wherein said heat treatment step (iv) is carried out at 90°–130° C. for 0.2–24 hours.

Item 17. The method for producing surgical suture according to item 13 wherein said relaxation treatment step (v) is carried out at 60°–110° C. for 0.2–20 hours.

The surgical suture comprises a copolymer consisting of lactic acid (lactide) and ε-caprolacton as essential repeating unit. Said copolymer is preferably a copolymer consisting of lactic acid (lactide) and ε-caprolacton, but may include other repeating units as long as the other repeating units do not impart serious adverse effects on properties of copolymer, such as uniformness, shrinkage, knot-pull strength, tensile strength, tensile elongation at break, knot elongation at break, etc. Such repeating units are preferably bioabsorbable, such as glycolic acid, trimethylenecarbonate, dioxanone, etc.

The surgical suture of the invention preferably consists of said copolymer, but may include other copolymer, as long as the other copolymer does not impart serious disadvantage to properties of suture, such as uniformness, shrinkage, knot-pull strength, tensile strength, tensile elongation at break, knot elongation at break, etc. Examples of such copolymer are polyglycolic acid, polylactic acid (polylactide), polycaprolacton, etc.

A blending ratio of lactide and ε-caprolacton is, when taking total molar amount of lactide and ε-caprolacton as 100 mole %, lactide:ε-caprolacton=99.9–50 mole %:0.1–50 mole %; preferably 90–75 mole %:10–25 mole %; more preferably 87–82 mole %:13–18 mole %.

L-lactide, D-lactide and DL-lactide (lacemic modification) may be used as lactide. L-lactide is preferably used as lactide.

The quality of the surgical suture of the invention is uniform, because the suture is prepared by uniform drawing in hot water bath with constant temperature after melt spinning.

Molecular weight of copolymer, which is a constituent of surgical suture of the invention, composed of lactide and ε-caprolacton as repeating unit ranges from about 100.000 to 300.000, preferably about 150.000 to 250.000, more preferably about 180.000 to 250.000 provided that the molecular weight is determined by GPC (gel permeation chromatography).

Preferable properties of surgical suture of the invention are shown below:

(1) shrinkage ratio (60° C., 20 min)=about 5.0% or less, preferably about 3.0% or less;

(2) tensile strength=about 2.5 g/d or more, preferably about 2.5 to 4.5 g/d;

(3) knot-pull strength=about 2.0 g/d or more, preferably about 2.0 to 2.5 g/d;

(4) tensile elongation at break=about 50±10%, preferably about 50±5%; and (5) knot elongation at break=about 45±10%, preferably about 45±5%.

The surgical suture of the invention may be composed of monofilament or multifilament, preferably monofilament to decrease risk of bacterial infection.

The suture of the invention may be produced according to the following steps.

(Step A) Melt spinning and Drawing in hot water

As shown in FIG. 1(A), a copolymer consisting of lactide and ε-caprolacton as repeating unit is melt-spinned. Melt spinning is carried out by conventional methods. Specifically, melt spinning is carried out at temperature of about 170°–240° C. Molecular weight of copolymer subjected to melt spinning step is not specifically limited to, but usually ranges from about 150.000 to 500.000, preferably about 250.000 to 350.000.

Filament melt-spinned is subjected to drawing step in hot water.

In the drawing step in hot water, temperature of water bath usually ranges from about 60°–90° C., preferably 70°–80° C. Draw ratio depends on temperature of water bath, but usually ranges from about 8 to 12, preferably about 9 to 10.

(Step B) Redrawing

Figure 1B:
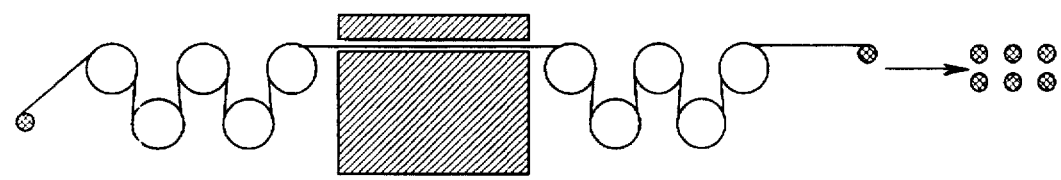

As shown in FIG. 1(B), tensile strength of filament prepared by drawing in water is not sufficient as surgical suture, the filament is redrawed to improve tensile strength thereof. Redrawing may be carried out according to a variety of known drawing steps in heating unit, such as drawing on hot roller, drawing in oven chamber, etc, preferably drawing in oven chamber with respect to uniformity of length. Drawing conditions are not specifically limited to. Drawing may be carried out, for example, at temperature of about 90°–140° C. under draw ratio of about 1.2–2.5; preferably at temperature of about 110°–130° C. under draw ratio of about 1.5–1.7.

(Step C) Heat treatment with tension

Figure 1C:
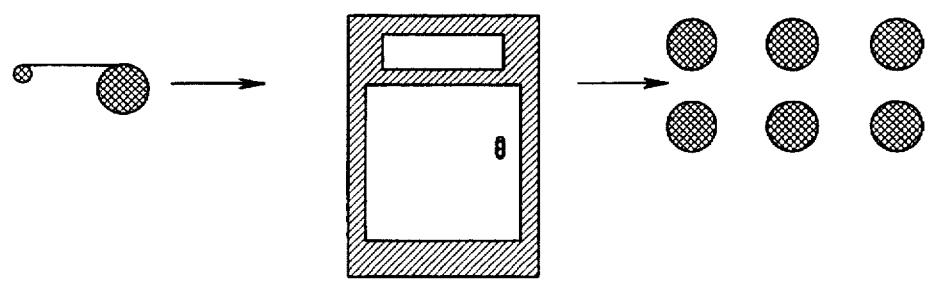
Figure 1D:
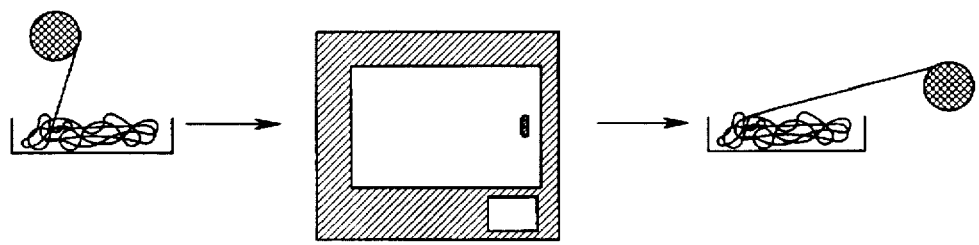

As shown in FIG. 1(C), a filament prepared according to step (A), followed by step (B) is subjected to heat treatment step. The heat treatment step is carried out with tension so as not to shrink the filament (without change in length). Specifically, heat treatment is carried out at about 90°–130° C. for about 0.2–24 hours, more preferably at about 110°–125° C. for about 0.5–8 hours under condition that filament is a bobbin. Heat-treatment time is shortened when temperature is elevated.

(Step D) Relaxation treatment

As shown in FIG. 1 (Step D), relaxation treatment may be carried out after heat treatment of step (C). The relaxation treatment may be carried out by treating filament in thermostatic chamber at about 60°–110° C. for about 0.2–20 hours, more preferably at about 60°–80° C. for about 4–20 hours. The relaxation treatment is usually carried out without tension so as not to inhibit shrinkage of filament by the relaxation treatment.

According to the invention, surgical suture with high knot-pull strength, flexible and smooth handling leading to ease of knot formation and a good knot security may be provided. In addition, according to the method of the invention, such surgical suture may be produced with low costs.

BEST MODE FOR CARRYING OUT THE INVENTION

The present invention will be described in detail with examples. However, the invention is in no way limited by the examples.

EXAMPLE 1

Surgical sutures composed of monofilament was obtained by treating samples 1 and 2 made of copolymer of L-lactide and ε-caprolacton (L-lactide:ε-caprolacton=85.5 mole %:14.5 mole %; Molecular Weight determined by GPC= about 250.000) according to the steps of melt spinning, drawing in hot water, redrawing, heat treatment and relaxation treatment under the following conditions.

(1) Melt spinning

Melt temperature=185° C.

(2) Drawing in hot water

Temperature of hot water=75° C.

Draw ratio=9

(3) Redrawing

Temperature of oven chamber for drawing=130° C.

Draw ratio=1.67

(4) Heat treatment

Temperature of thermostatic chamber=115° C.

Treatment time=20 hours (5) Relaxation treatment with no shrinkage of filament

Temperature of thermostatic chamber=60° C.

Treatment time=20 hours

Shrinkage ratio, tensile strength, knot-pull strength, elongation at break of each filament after each step of melt spinning, drawing in hot water, redrawing, heat treatment and relaxation treatment are shown in table 1 below. Testing of strength and elongation was carried out with strength and tensile tester under conditions of distance between set of chucks=10 cm; and crosshead speed=10 cm/min. Knot-pull strength and elongation test was carried out according to "Regulation of plastic suture" Notification No.444 of the Ministry of Health and Welfare, Japan as defined in pharmaceutical affairs law. Data in tables 1 and 2 were determined after the following conditions.

Condition (A): after drawing in hot water;

Condition (B): after redrawing;

Condition (C): after heat treatment with tension;

Condition (D): after relaxation treatment; and

Condition (E): after gas sterilization treatment with ethyleneoxide (EO) (60° C., 24 hours)

In addition, in tables 1 and 2, shrinkage ratio after treatment at 60° C., for 20 hours was calculated according to the following equation.

$$\text{Shrinkage ratio } (\%) = (L - L_1)/L \times 100$$

L=length before treatment;

$L_1$=length after treatment.

The relationship between temperature and shrinkage ratio (%) after treatment of steps (A) to (D) with respect to samples 1 and 2 is shown below.

EXAMPLE 2

Surgical sutures consisting of monofilament was obtained by treating sample 3 made of copolymer of L-lactide and ε-caprolacton (L-lactide:ε-caprolacton=82.5 mole %:17.5 mole %; Molecular Weight determined by GPC=about 260,000) according to the steps of melt spinning, drawing in hot water, redrawing, heat treatment and relaxation treatment under the following conditions.

(1) Melt spinning

Melt temperature=185° C.

(2) Drawing in hot water

Temperature of hot water=80° C.

Draw ratio=9

(3) Redrawing

Temperature of oven chamber for drawing=120° C.

Draw ratio=1.67

(4) Heat treatment

Temperature of thermostatic chamber=90° C.

Treatment time=16 hours (5) Relaxation treatment with no shrinkage of filament

Temperature of thermostatic chamber=60° C.

Treatment time=20 hours

Size of filament (denier, diameter), tensile strength and elongation at break; knot-pull strength and elongation at break; and shrinkage ratio of monofilament after steps (A) to (D) are shown in table 2 below.

EXAMPLE 3

Surgical sutures composed of monofilament was obtained by treating sample 4 made of copolymer of L-lactide and ε-caprolacton (L-lactide:ε-caprolacton=87.5 mole %:12.5 mole %; Molecular Weight determined by GPC=about 425,000) according to the steps of melt spinning, drawing in hot water, redrawing, heat treatment and relaxation treatment under the following conditions.

(1) Melt spinning

Melt temperature=185° C.

(2) Drawing in hot water

Temperature of hot water=80° C.

Draw ratio=9

(3) Redrawing

Temperature of oven chamber for drawing=130° C.

Draw ratio=1.67

(4) Heat treatment

TABLE 1

| Condition | Size of filament | | Tensile | | | Knot | | | Shrinkage |
|---|---|---|---|---|---|---|---|---|---|
| | Denier (d) | Diameter (mm) | tenacity (g) | strength (g/d) | elongation (%) | tenacity (g) | strength (g/d) | elongation (%) | ratio (%) |
| Sample 1 | | | | | | | | | |
| (A) | 2913 | 0.578 | 7574 | 2.60 | 40.5 | 5418 | 1.86 | 38.0 | 25.5 |
| (B) | 1748 | 0.448 | 7680 | 4.39 | 30.0 | 4055 | 2.32 | 26.1 | 24.1 |
| (C) | 1726 | 0.444 | 6017 | 3.49 | 30.1 | 3159 | 1.83 | 23.8 | 12.4 |
| (D) | 1946 | 0.463 | 7153 | 3.68 | 51.4 | 4281 | 2.20 | 39.6 | 0.9 |
| (E) | 1950 | 0.465 | 7176 | 3.68 | 52.5 | 4428 | 2.27 | 41.5 | 0.3 |
| Sample 2 | | | | | | | | | |
| (A) | 3273 | 0.608 | 8837 | 2.70 | 36.4 | 5531 | 1.69 | 34.1 | 26.1 |
| (B) | 1964 | 0.471 | 8457 | 4.31 | 26.3 | 3450 | 1.76 | 17.5 | 24.5 |
| (C) | 1889 | 0.458 | 8020 | 4.25 | 27.0 | 3495 | 1.85 | 16.9 | 11.0 |
| (D) | 2108 | 0.485 | 7909 | 3.75 | 41.8 | 4532 | 2.15 | 31.6 | 1.4 |
| (E) | 2097 | 0.491 | 8579 | 4.09 | 45.3 | 4446 | 2.12 | 34.0 | 0.2 |

Temperature of thermostatic chamber=100° C.

Treatment time=16 hours (5) Relaxation treatment with no shrinkage of filament

Temperature of thermostatic chamber=60° C.

Treatment time=20 hours

Size of filament (denier, diameter); tensile strength and elongation at break; knot-pill strength and elongation at break; and shrinkage ratio of monofilament after steps (A) to (D) are shown in table 2 below.

TABLE 2

| | Size of filament | | Tensile | | | Knot | | | Shrinkage |
|---|---|---|---|---|---|---|---|---|---|
| Condition | Denier (d) | Diameter (mm) | tenacity (g) | strength (g/d) | elongation (%) | tenacity (g) | strength (g/d) | elongation (%) | ratio (%) |
| Sample 3 | | | | | | | | | |
| (A) | 1043 | 0.343 | 3807 | 3.65 | 37.4 | 2378 | 2.28 | 29.7 | 38.7 |
| (B) | 802 | 0.301 | 3112 | 3.88 | 33.0 | 1869 | 2.33 | 34.1 | 18.3 |
| (C) | 791 | 0.296 | 3006 | 3.80 | 38.7 | 1709 | 2.16 | 30.6 | 19.3 |
| (D) | 949 | 0.334 | 2676 | 2.82 | 65.0 | 1983 | 2.09 | 55.0 | 0.7 |
| (E) | 954 | 0.332 | 2748 | 2.88 | 63.5 | 2013 | 2.11 | 56.1 | 0.2 |
| Sample 4 | | | | | | | | | |
| (A) | 824 | 0.301 | 2983 | 3.62 | 33.4 | 1747 | 2.12 | 24.6 | 21.6 |
| (B) | 561 | 0.246 | 2143 | 3.82 | 33.0 | 1105 | 1.97 | 21.3 | 9.3 |
| (C) | 540 | 0.234 | 2192 | 4.06 | 34.1 | 1188 | 2.20 | 23.3 | 4.7 |
| (D) | 566 | 0.247 | 1964 | 3.47 | 37.0 | 1171 | 2.07 | 27.0 | 0.5 |
| (E) | 571 | 0.249 | 1959 | 3.43 | 36.5 | 1199 | 2.10 | 27.4 | 0.3 |

As shown in the tables 1 and 2, sutures obtained in examples 1–3 are suitable as surgical suture because of having a good knot-security, flexibility and smooth handling thereof.

Figure 2:
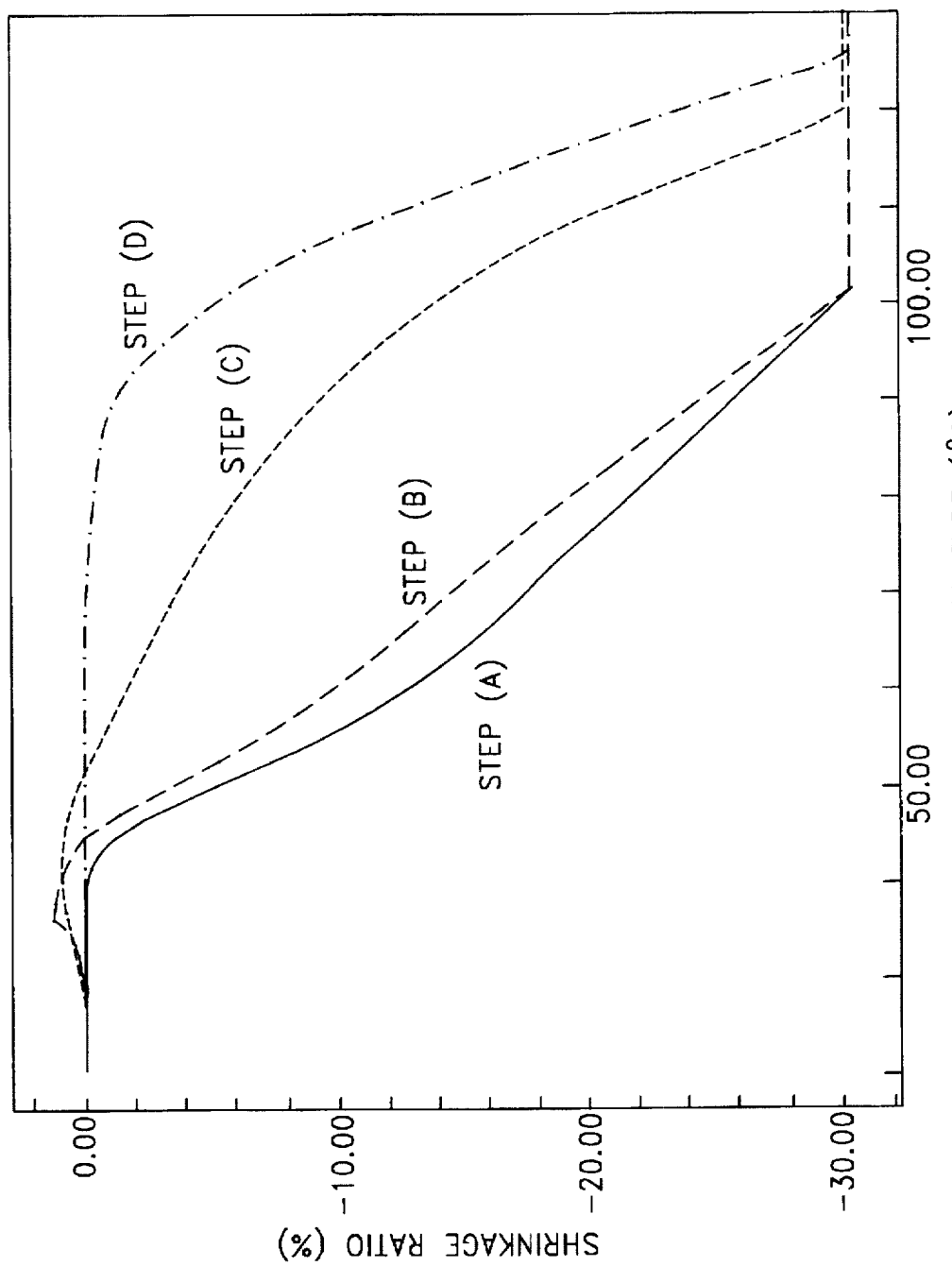
FIG. 2 is a graph showing relationship between temperature of treatment of steps (A) to (D) and shrinkage ratio (%).
Figure 3:
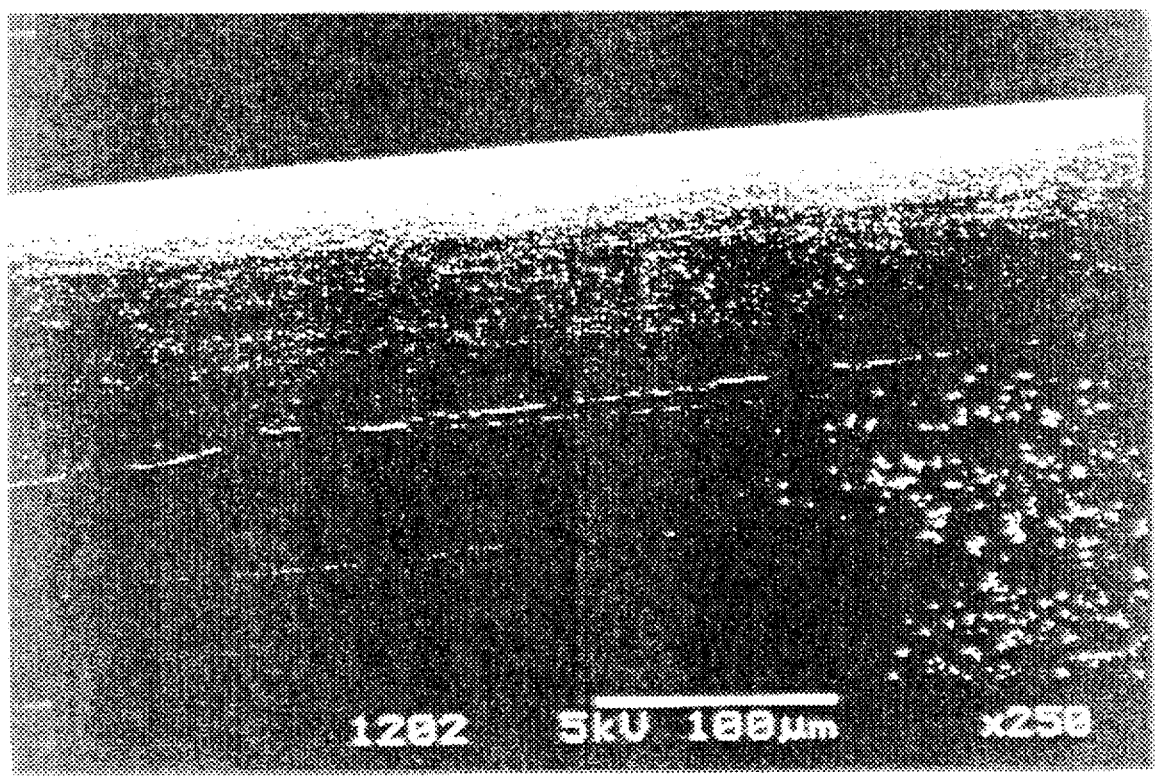
FIG. 3 is a copy of surface scaling up photograph showing shape of filament prepared after condition (E) of sample 1.

A copy of scaling up photograph (FIG. 3) attached hitherto, which is a 250-fold scaled up photograph on the surface of sample 1, condition (E) in example 1. FIG. 2 demonstrates change of shrinkage behavior by heat treatment after each step, i.e., by heat treatment at various temperature after steps (A) to (D). As shown in FIG. 2, suture sample of the invention treated according to step (D) has substantially no change in length at about 100° C. or less.

We claim:

1. A surgical suture comprising a copolymer of lactic acid or lactide and ε-caprolacton in an amount sufficient to reduce the shrinkage ratio of said surgical suture to 5% or less when treated at 60° C. for 20 hours.

2. The surgical suture according to claim 1 wherein molecular weight of said suture determined by GPC ranges from about 100,000 to 250,000.

3. The surgical suture according to claim 1, wherein a mole percentage of said lactic acid or lactide is about 99.9-50 mole % and the mole percentage of said ε-caprolacton is about 0.1–50 mole %, based on the total moles of said lactic acid or lactide and said ε-caprolacton.

4. The surgical suture according to claim 1 wherein tensile strength of said suture is at least 2.5 g/d.

5. The surgical suture according to claim 1 wherein knot-pull strength of said suture is at least 2.0 g/d.

6. The surgical suture according to claim 1 wherein elongation at break of said suture is 50±10%.

7. The surgical suture according to claim 1 wherein knot-pull elongation at break of said suture is 45±10%.

8. The surgical suture according to claim 1, wherein said suture is in the form of a monofilament.

9. The surgical suture according to claim 1, wherein said suture is in the form of a multifilament.

10. A method for producing a surgical suture, comprising the steps of:

(i) melt-spinning a copolymer of lactic acid or lactide and ε-caprolacton; and (ii) drawing the melt-spun copolymer of step (i) in hot water.

11. The method for producing surgical suture according to claim 10, further comprising the step of:

(iii) redrawing the copolymer drawn in step (ii).

12. The method for producing a surgical suture according to claim 11 wherein said redrawing step (iii) is carried out at 90°–140° C. under draw ratio of 1.2–2.5.

13. The method for producing a surgical suture according to claim 11, further comprising the step of:

(iv) heating the redrawn copolymer of step (iii).

14. The method for producing a surgical suture according to claim 13 wherein said heat treatment step (iv) is carried out at 90°–130° C. for 0.2–24 hours.

15. The method for producing a surgical suture according to claim 13, comprising the step of:

(v) relaxing the resulting copolymer of step (iv).

16. The method for producing a surgical suture according to claim 15 wherein said relaxation treatment step (v) is carried out at 60°–110° C. for 0.2–20 hours.

17. The method for producing a surgical suture according to claim 10 wherein said drawing step (ii) in hot water is carried out at 60°–90° C. at a draw ratio of 8–12.

18. A method for suturing an open wound of a patient, comprising the steps of suturing said open wound using a surgical suture comprising a copolymer of lactic acid or lactide and ε-caprolacton in an amount sufficient to reduce the shrinkage ratio of said surgical suture to 5% or less when treated at 60° C. for 20 hours; and knotting said suture.

* * * * *